United States Patent
Susil et al.

(10) Patent No.: US 7,225,012 B1
(45) Date of Patent: May 29, 2007

(54) METHODS AND SYSTEMS FOR IMAGE-GUIDED SURGICAL INTERVENTIONS

(75) Inventors: Robert Charles Susil, Baltimore, MD (US); Russell H. Taylor, Severna Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 468 days.

(21) Appl. No.: 09/663,989

(22) Filed: Sep. 18, 2000

(51) Int. Cl.
*A61B 5/00* (2006.01)

(52) U.S. Cl. .................. 600/414; 600/407; 600/410; 600/411

(58) Field of Classification Search ........ 600/407–482; 606/130; 601/1–5
See application file for complete search history.

(56) References Cited

U.S. PATENT DOCUMENTS

| | | | | |
|---|---|---|---|---|
| 4,938,220 A | 7/1990 | Mueller, Jr. | ................ | 128/658 |
| 5,097,839 A | 3/1992 | Allen | ................ | 128/653.1 |
| 5,142,930 A | 9/1992 | Allen et al. | ................ | 74/469 |
| 5,178,164 A | 1/1993 | Allen | ................ | 128/898 |
| 5,222,499 A | 6/1993 | Allen et al. | ................ | 128/653.1 |
| 5,230,338 A | 7/1993 | Allen et al. | ................ | 128/653 |
| 5,318,025 A * | 6/1994 | Dumoulin et al. | ................ | 600/417 |
| 5,397,329 A | 3/1995 | Allen | ................ | 606/73 |
| 5,445,151 A * | 8/1995 | Darrow et al. | ................ | 128/653.3 |
| 5,572,999 A | 11/1996 | Funda et al. | ................ | 128/653.1 |
| 5,776,064 A * | 7/1998 | Kalfas et al. | ................ | 600/414 |
| 5,782,764 A | 7/1998 | Werne | ................ | 600/411 |
| 5,797,849 A | 8/1998 | Vesely et al. | ................ | 600/461 |
| 5,871,445 A * | 2/1999 | Bucholz | ................ | 600/407 |
| 5,947,981 A | 9/1999 | Cosman | ................ | 606/130 |
| 5,951,475 A * | 9/1999 | Gueziec et al. | ................ | 600/425 |
| 5,999,840 A | 12/1999 | Grimson et al. | ................ | 600/424 |
| 6,132,437 A * | 10/2000 | Omurtag et al. | ................ | 606/130 |
| 6,206,890 B1 * | 3/2001 | Truwit | ................ | 606/130 |
| 6,272,370 B1 * | 8/2001 | Gillies et al. | ................ | 600/411 |
| 6,304,769 B1 * | 10/2001 | Arenson et al. | ................ | 600/424 |
| 6,379,302 B1 * | 4/2002 | Kessman et al. | ................ | 600/437 |
| 6,381,485 B1 * | 4/2002 | Hunter et al. | ................ | 600/407 |

FOREIGN PATENT DOCUMENTS

| | | |
|---|---|---|
| EP | 0 640 842 A1 | 3/1995 |
| WO | WO 99/58069 | 11/1999 |
| WO | WO 00/07652 | 2/2000 |

* cited by examiner

*Primary Examiner*—Brian L. Casler
*Assistant Examiner*—William C Jung
(74) *Attorney, Agent, or Firm*—Peter F. Corless; Lisa Swiszcz Hazzard; Edwards Angell Palmer & Dodge LLP

(57) ABSTRACT

Featured is a system to determine the three-dimensional position and orientation of an effector (a needle, probe, or other medical instrument) relative to a subject using cross-sectional images (e.g. from a CT or MRI scanner). Also provided is a method for image guided effector placement that requires no immobilization of the patient or fiducial implantation. A localization module (fiducial object) is integrated or associated with the effector allowing for the localization of the effector in the image space using a single cross-sectional image.

37 Claims, 3 Drawing Sheets

METHODS AND SYSTEMS FOR IMAGE-GUIDED SURGICAL INTERVENTIONS

BACKGROUND OF THE INVENTION

1. Field of the Invention

The present invention relates to methods and systems for image-guided effector placement. Methods and systems of the invention enable minimally invasive image-guided interventions with a single cross-sectional image and without the use of a sterotactic frame or separate fiducial apparatus. Preferred systems of the invention include a localization module, integrated with a medical instrument, that allows for localization of the effector in targeted image space using a single cross-sectional image.

2. Background

Percutaneous procedures, i.e. through the skin procedures, require one to find the position of an internal target, e.g. organ, tumor, etc., without direct visualization. Most often, this involves registration of an image data set, in which the target is identified, with physical space. This procedure, stereotaxy, was reported early by Clarke and Horsley (Clarke, *Brain* (1905) 28:12-29). Most techniques have been based upon the attachment of a rigid frame to a patient, providing a common coordinate system through which the image and physical spaces can be related (Galloway, in *Interactive Image-Guided Neurosurgery. American Association of Neurologic Surgeons* (1993) 9-16). While stereotactic procedures were initially advanced using two-dimentional imaging modalities, the advent of three dimensional imaging systems including Computed Tomography (CT) in the 1970's greatly accelerated development and applications. Instead of projecting three-dimensional structures into two-dimensions, this modality provides a series of 2D image slices, allowing for true three-dimensional reconstruction.

The Brown-Roberts-Wells (BRW) frame consisting of three N shaped motifs attached to a patient's skull, represented a major advance in localization (Brown, *Invest Radiol* (1979) 14:300-304). Previous frames were constrained to remain strictly perpendicular to the image plane, providing little flexibility (Galloway, in *Interactive Image-Guided Neurosurgery. American Association of Neurologic Surgeons* (1993) 9-16). However, the BRW frame was more versatile in that the position and orientation of the frame was fully encoded within each image slice such that the position of a point was defined in both the frame space and the image space coordinate systems allowing for rotations and tilting of the frame relative to the image plane (Brown, *Invest Radiol* (1979) 14:300-304).

A number of systems use a rigid stereotaxic frame wherein the frame is attached to the patient. These devices tend to be large and unwieldy contraptions that limit the effective application time of the frame to less than a day. Consequently, the frame must be recalibrated before each use. A system was implemented for image guide intracranial needle placement using biplanar x-ray and a fixed head frame (Lavallee, *Computer Integrated Surgery: Technology and Clinical Applications*, (1996) p 343-351). In another neurosurgical system, a surgical plan using multiple CT image slices, register by docking their robot with the patient's stereotactic head frame, and then place the needle without CT surveillance (Kwoh, *IEEE Trans Biomed Eng* (1988) 35:153-160). In another system a stereotactic head frame is used to register the robot and image space, but are able to perform needle placement under active CT surveillance to confirm the position of their end effector (Glauser, *Second Annual International Symposium on MRCAS* (November 1995)). Similarly, a method wherein the placement and register of a needle under biplanar fluoroscopy, was developed in order to access mobile organs (e.g. the kidneys) (Bzostek et al. *The First Joint Conference of CVRMed and MRCAS*, (March 1997) Grenoble, France).

Surgically implanted fiducial markers have been employed to generate reference frame in the patient and have been affixed to the bones, in particular the cranium, to prevent the marker from shifting with time. These implant systems have been used for image-guided applications in the brain where the cranium is readily accessible for surgical implantation of fiducial markers. Surgical pins and screws for permanently affixing fiducial implants to a patient bone are reported in U.S. Pat. Nos. 5,397,329 and 5,636,255 such that pegs, pins or screws comprising a scanner opaque object are surgically implanted into one or more bones such as the cranium, sternum or vertabrae. Fiducial markers that are implanted into the patient's soft tissue are reported in U.S. Pat. Nos. 5,941,890 and 6,056,700.

While these implanted markers are fixed within the body and are unlikely to move, there are several drawbacks to their use. Implantation requires surgery wherein the markers are inserted or driven into the bones raising the concern of cracking or otherwise damaging the support bone in the implantation process. Further surgical procedures increase patient discomfort, hospital stays or recovery time and the risk of complications such as infection or bone damage.

It thus would be desirable to have improved methods and systems to determine the location of an end effector delivery system and the location of an effector such as a needle, probe, etc. within a body. It would be further desirable to have such a position and orientation system that could be employed in minimally invasive surgical procedures without need for external reference frames, surgically implanted fiducial markers or calibration procedures.

SUMMARY OF THE INVENTION

We have now discovered image registration systems for determining the three-dimensional position and orientation of a medical instrument (effector) such as a needle, probe, etc. relative to a subject using one or more cross sectional images of the subject. Significantly, methods and systems of the invention enable effector placement without use of patient immobilization or separate fiducial implantation.

More particularly, we have discovered that by placement of a fiducial object separate from a patient but in association with a medical instrument, a single cross-sectional image can be taken via an imaging device such as Computed Tomography, Magnetic Resonance Imaging or ultrasound, and that single image employed to directly manipulate and orient the medical instrument during the course of a surgical procedure.

That is, the invention includes use of an imaging system that comprises an imaging apparatus and a medical instrument with an associated fiducial object that can be imaged in the same image (cross-sectional image) as a targeted site of the patient (e.g. a tumor, organ, etc.); a medical image (cross-sectional image) is obtained that comprises both the fiducial object and the targeted site of the patient; and manipulating the instrument with respect to the patient using information derived from the image.

It should be appreciated that the systems and methods of the invention enable direct manipulation of a medical instrument based on a cross-sectional image.

Thus, the systems and methods of the invention enable calculating, relating and manipulation of the position of the medical instrument and target site of a patient (e.g. tumor, site for drug delivery, etc.) via the information contained in a single cross-sectional image. Prior approaches have required use of multiple reference frames to calculate relative positions of a medical instrument and a targeted site of a patient, e.g. an image is taken of a target site and a separate fiducial implant and that reference frame related to the separate reference frame in which the medical instrument is positioned, which relation requires use of a third reference frame or overlay of the first and second reference frames. Clearly, the methods and systems of the invention are a significant advance which can effectively utilize a single reference frame to calculate, relate and manipulate relative positions of the medical instrument and target site of a patient.

Image registration systems of the invention system preferably comprise an imaging device, e.g. a scanning device such as a computed topography (CT) or magnetic resonance imaging (MRI) scanner or an imaging ultrasound device. The imaging device is in communication with a surgical instrument, e.g. an effector such as a needle, probe, drug delivery device, and the like. The medical instrument has an associated fiducial object (e.g. localization module) that enables generating three identifiable points via a cross-sectional image to coordinate pose of the instrument with respect to a targeted site of the patient. The fiducial object may be e.g. integral to the instrument, or attached or otherwise affixed to the instrument. The fiducial object also may be separate from the instrument but nevertheless associated therewith provided the fiducial object and the instrument maintain a fixed spatial relationship.

The imaging device typically is in communication with one or more surgical instruments and can provide substantially contemporaneous communication of data provided by the imaging and corresponding manipulation of the instrument(s). That is, the apparatus and methods of the invention provide an active registration system whereby a subject is being imaged, e.g. positioned within a CT or MRI scanner, permitting direct and substantially contemporaneous visualization and confirmation of the location of effector, and anatomical structures during effector placement.

The imaging device yields a cross-sectional image that provides three identifiable points on the insector plane between the targeted site (e.g. lesion, tumor, site of drug delivery) and the surgical instrument. Those three identified points, obtained via a single cross-sectional image, can enable high precision manipulation of the instrument. That is, image registration systems of the invention can allow for a precise localization of the effector in the image space relative to the subject using a single cross-sectional image.

Multiple cross-sectional images also can be employed, particularly to enhance accuracy (e.g. by averaging multiple images) and to compensate for patient motion during the course of a surgical procedure. The multiple images are typically obtained over a period of time, e.g. at least about one or two minutes, or over the course of about three, four, five or more minutes. A volumetric image also may be obtained. Multiple images also may be obtained quite rapidly, e.g. multiple images obtained each second, and such rapid imaging extended over the course of a medical procedure.

Image guidance systems of the invention are advantageously employed in percutaneous surgical procedures for localized therapy delivery and diagnostic biopsy, with distinct advantages over prior percutaneous placement techniques. For example, while previous techniques have relied on methods that only register the device space once; the active single image guidance system is able to perform a registration for every scanned image slice. The effector (medical instrument) and patient are contained within the cross sectional imager such that images can be taken at any point for confirmation of effector location. An operator can then directly visualize and confirm when an effector such as a needle, probe, etc. has reached the desired target. In addition, image guidance can be employed to avoid contacting or otherwise damaging sensitive structures (such as vascular tissue). In soft tissues, such as the liver, monitoring progress with additional scanned images allows the operator to adjust the target and effector trajectory to compensate for tissue deformation. This allows for frequent positive confirmation of position and pose of the effector that is a significant safety advantage. Specific applications of percutaneous procedures include but are not limited to prostate biopsy and therapy delivery, access to the spine and liver biopsy.

The systems and methods of the invention provide significant additional advantages. Systems of the invention can effect controlled, well-planned movements of the effector with high localization accuracy and error attenuation over a large range of positions and orientations such that the risk of inadvertent motion is minimized. In addition, when using imaging modalities that involve ionizing radiation (such as CT), robotic positioning of the effector can reduce or eliminate operator (e.g. physician, technician, etc.) exposure to harmful emissions. This system is markedly less invasive than previous techniques whereby surgical morbidity, patient discomfort and duration of recovery time/hospitalization are reduced.

Systems and methods of the invention can be employed for a wide variety of therapeutic regimes. For example, a variety of materials deposited or administered to the patient by the systems and methods of the invention, such as therapeutic agents e.g. chemotherapeutics, DNA therapeutics (gene therapy), radiation seed implant, antibacterial agent, and the like; ethanol; a sclerotic solution; energy such as e.g. high intensity ultrasound, directed beam therapy, localized X-ray therapy, photodynamic therapy, laser ablation therapy, RF ablation therapy, and the like; energy removal from a patient such as cryotherapy; tissue removal such as removal of a tumor, biopsy sample, etc.

Other aspects of the invention are discussed infra.

DETAILED DESCRIPTION OF THE INVENTION

As discussed above, a registration system is provided for determining the three-dimensional position and orientation of an effector such as a needle, probe, etc. relative to a subject using one or more cross sectional images of the subject. The image registration system suitably comprises a scanning device such as a CT, MRI or the like, and a fiducial object (i.e. that can be detected by the imaging apparatus) associated with a surgical instrument. Systems and methods of the invention enable effector placement without use of patient immobilization or separate fiducial implantation.

In particular, systems and methods of the invention provide a fiducal object representation in a single cross-sectional image that is unique for the pose of the instrument within the therapeutic field (i.e. the targeted treatment area of the patient) or range of motion of the medical instrument with which the fiducial object is associated.

By stating that a fiducial object is associated with a medical instrument (e.g. probe, needle/needle driver, etc.), it is indicated that the fiducial object is an integral component of the medical instrument, attached to the medical instrument (e.g. by adhesive, etc.), or where the fiducial object is separately (without physical attachment) positioned from the medical instrument but the medical instrument and the fiducial object maintain a fixed relationship.

Figure 1:
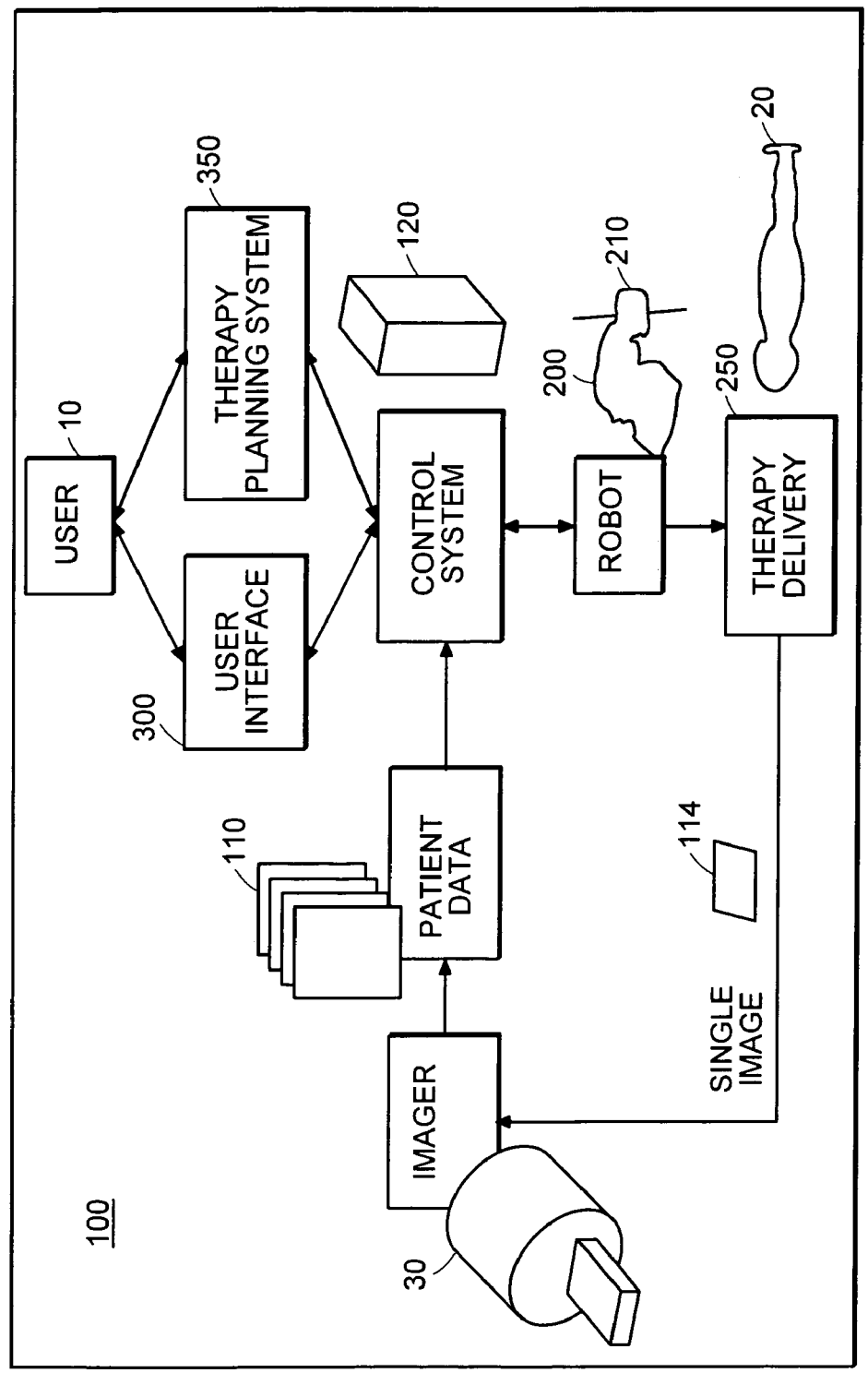
FIG. 1 shows schematically a preferred image registration system and operation cycle thereof of the invention. Data is made available to both the user and a therapy planning system to provide a treatment plan. Therapy is executed via a robotically controlled end effector.

Referring now to the various figures of the drawing wherein like reference characters refer to like parts, FIG. 1 schematically illustrates one preferred embodiment 100 of single registration system in accordance with the present invention. Here, a patient 20 is located within an imager 30 whereby patient image data 110 is collected and transferred to a control apparatus 120. A user interface 300 interacts with the control apparatus 120 to display localization information and to receive information from the user. The therapy planning unit 350 also interacts with the control system 120 and the user 10 to arrive at a treatment plan. The control apparatus 120 directs a robotic end effector 200 that controls a therapy delivery unit 250 located within the imager 30. A fiducial object (localization device) 210 is mounted on the end effector 200. The progress of the therapy delivery unit 250 in applying the treatment plan can be monitored in real-time by imager 30 feedback wherein the position of the therapy delivery unit 250 is determined relative to the target from a single image 114 comprising a cross section of the patient 20, the therapy delivery unit 250 and the localization device 210.

The robotic end effector 200 comprises a mounting site for the fiducial object 210, a device to hold an effector or therapy delivery unit 250 such as a needle, probe, etc. and a robotic arm or other device that is capable of translating the held effector in three dimensions with a relatively wide range of motion, e.g. at least 3 degrees of motion, more preferably at least about 4, 5, 6, 7, 8, 9 or 10 degrees of motion. Preferably, the robotic arm has at least 4 or more preferably at least about 5 degrees of motion such that the held effector can be located at any specified physical location in any specified orientation.

In order to register the therapy delivery unit 250 to the image space, the control system 120 has to identify a set of three corresponding points in both the robotic end effector 200 (holder) coordinate system, H, and the image coordinate system, I. These three points define a coordinate system P.

By finding the position and orientation of P in the image space, $^I_PT$, and the holder space, $^H_PT$, the control system 120 can then determine the pose of the robotic end effector (holder) in the image coordinate system, $^I_HT = ^I_PT(^H_PT)^{-1}$. The calibration of the robotic end effector 200 (holder), H, and the therapy delivery unit 250 (needle), N, coordinate systems $^H_NT$, were previously performed whereby the control apparatus 120 can find $^I_NT$, the pose of therapy delivery unit 250 (needle) in the image space.

In order to find the set of three corresponding points in both the image and holder coordinate systems using only one cross sectional image, a fiducial object 210 is employed wherein the device uses the Brown-Roberts-Wells frame (Brown, *Invest Radiol* (1979) 14:300-4). The Brown-Roberts-Wells frame is merely illustrative and other approaches can be utilized that can uniquely identify three distinct points.

Figure 2A:
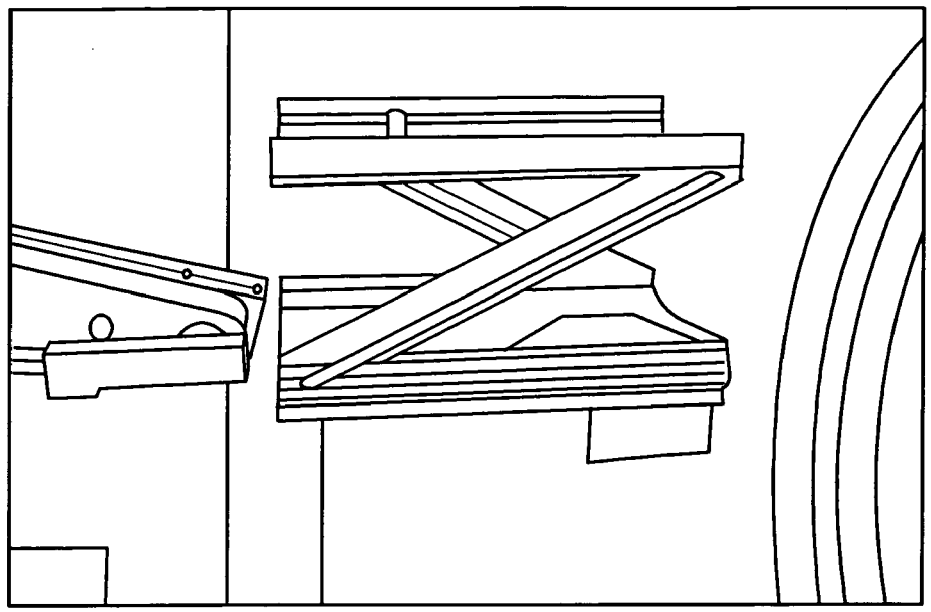
FIG. 2 (which includes FIGS. 2A and 2B) shows a preferred localization device attached to the end effector (medical instrument) for use in the systems and methods of the invention. When inserted into the image field of view, a cross section of each of the fidicual bars (nine) can appear in the scanning image (e.g. CT or MRI), allowing for registration.
Figure 2B:
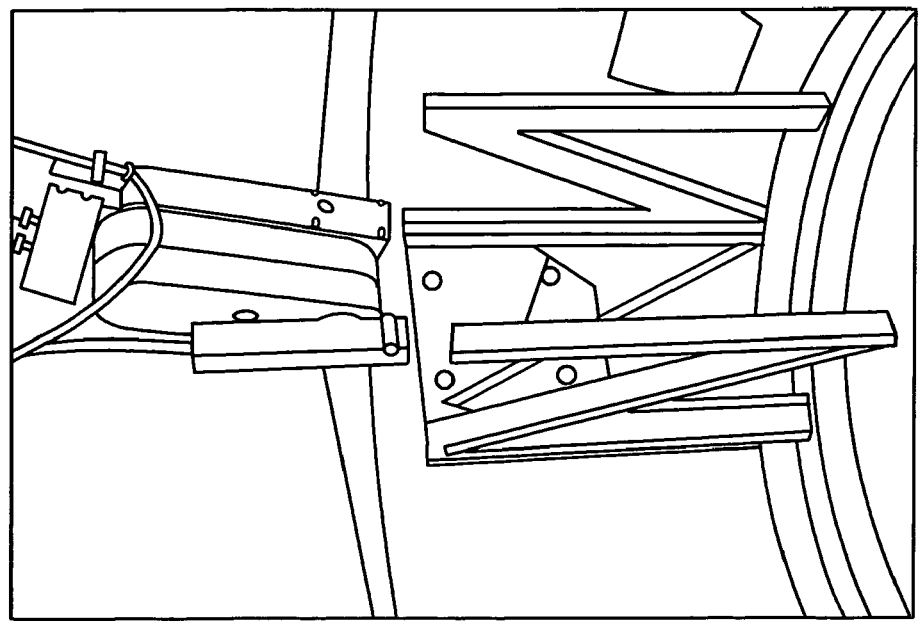
Figure 3A:
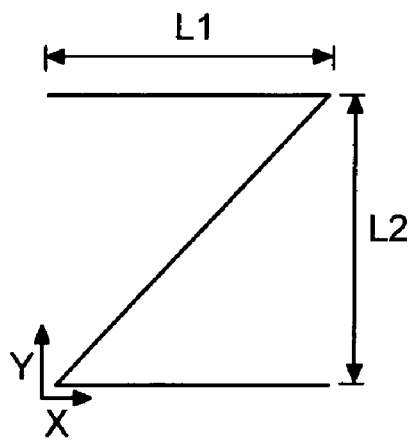
FIG. 3 (which includes FIGS. 3A and 3B) shows dimensioning and coordinate system conventions for fiducial motifs (FIG. 3A), and one fiducial motif intersected by the image plan, where p1, p2, and p3 are the three fiducial bar points of intersection with the image plan, and f, $\phi$ and $\theta$ define the orientation of the image plan relative to the fiducial motif (f=fraction of distance along the diagonal fiducial where intersection occurs) (FIG. 3B).

Now referring to FIG. 2, the basic structural element of the fiducial object 210 is a 'N' shaped fiducial motif 214. Preferably, this motif is repeated three times, forming a 'U' shaped module with one fiducial motif 214 as a base and the other two fiducial motifs as sides. The fiducial object 210 is attached to the robotic end effector 200 in such a way that the localization device is within the imager field of view. Preferably the localization device 210 is rigidly attached to the robotic end effector 200. More preferably the localization device 210 is attached using at least four screws. The material used for the fiducial motifs 214 is opaque to imager 30 radiation and they are supported by or embedded in a material that is transparent to imager 30 radiation. When the imager is a CT scanner, a metal rod is used for the fiducial motifs, preferably the metal rod is aluminum. More preferably the metal rod is aluminum with a diameter of from about 0.1 to about 0.5 inches, preferably a diameter of about 0.25 inches. The dimensioning ($L_1, L_2$) and coordinate system (x,y) for the fiducial motif 214 is illustrated in FIG. 3A. Preferably, $L_1$ is about 8 inches and $L_2$ is about 4 inches. However, other values of $L_1$ and $L_2$ will be appropriate for localization devices employed in different applications.

Figure 3B:
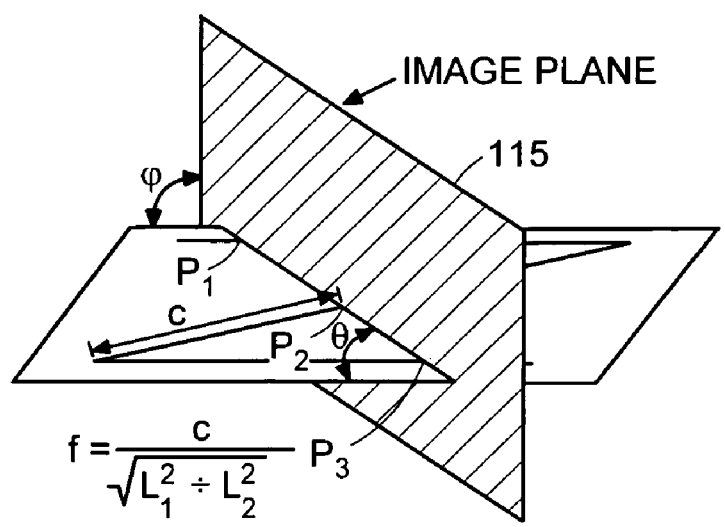

A schematic illustration of one fiducial motif 214 intersected by an image plane 115 is presented in FIG. 3B wherein $p_1$, $p_2$, $p_3$ are the three fiducial bar points of intersection with the image plane 115. The orientation of the image plane 115 relative to the fiducial motif 214 is described by three parameters by f, the fraction of the distance along the diagonal fiducial where the intersection occurs; $\phi$, the angle between the fiducial motif plane 214 and the image plane 115; and $\theta$, the angle between the parallel fiducial bars and the line of intersection.

The control apparatus 120 can process scanned images to relate the location and pose of the end effector and effector into the image coordinate system whereby a CT image of each fiducial motif produces a cross section of the three bars, yielding three ellipses in the image. By finding the centroids of these ellipses we can locate the centers of the three bars where they intersect the image plane $^IP1$, $^IP2$, and $^IP3$. Using these three points, the control apparatus 120 can determine the position of one corresponding point, $cp_n$, in both the holder space, $^Hcp_n$, and the image space $^Icp_n$. The control apparatus repeats this process for the remaining two fiducial motifs to generate all three corresponding points.

The distances $|FM_{P1}\_FM_{p2}|$ and $|FM_{P3}\_FM_{p2}|$, expressed as a function of f, φ, and θ, are:

$$|FM_{P1}\_FM_{p2}|=csc(\theta)L_2(1-f) \quad (1)$$

$$|FM_{P3}\_FM_{p2}|=csc(\theta)L_2(f) \quad (2)$$

The ratio of these distance expressed in equations (1) and (2) is:

$$\left|\frac{FM_{p1}\_FM_{p2}}{FM_{p3}\_FM_{p2}}\right| = \frac{1}{f} - 1 \quad (3)$$

The ratio (3) is only a function of f, the fraction of the distance along the diagonal fiducial where the intersection occurs. Because the transformation form the fiducial motif coordinate system to the image space is a rigid body transformation, the control apparatus 120 can determine the point where the image plane intersects the diagonal bar $FM_{p2}$, by finding the ratio of the distances between points $^Ip_1, ^Ip_2$, and $^Ip_3$. From a previous calibration of the robotic end effector 200 (holder), the control apparatus 120 knows the transformation for this point, $FM_{p2}$, to the holder coordinate system, $_{FM}^{H}T$. Therefore, control apparatus 120 knows the position of this intersection in both the image space $^Ip_2$, and the holder space $^Hp_2$, providing one of the three corresponding points, $cp_1$. The control apparatus 120 repeats this process for the two remaining fiducial motifs, generating all three corresponding points, $cp_1, cp_2$ and $cp_3$.

With the set of three point generated by the intersection of each of the three fiducial motifs and the image plane, the control apparatus 120 can do more than determine one corresponding point in the image holder coordinate systems. For example the control apparatus can further determine the angle θ (FIG. 3b), but there is very little accuracy in determining this angle. When operating about θ=90°, the sensitivity of our assessment of $\theta(\partial\theta_{measured}/\partial\theta_{actual})$ is zero. In contrast, determination of the corresponding point has much more attractive properties.

To robustly determine the corresponding points, the localization method must have two properties. First, the assessment of $^Hcp_n$ should be relatively insensitive to small measurement errors in $|^Ip_1-^Ip_2|$ and $|^Ip_3-^Ip_2|$. These sensitivities to measurement error are:

$$\frac{\partial c}{\partial |^Ip_1 - ^Ip_2|_{measured}} = -f\sqrt{1+\left(\frac{L_1}{L_2}\right)^2}\sin(\theta) \quad (4)$$

$$\frac{\partial c}{\partial |^Ip_3 - ^Ip_2|_{measured}} = -(1-f)\sqrt{1+\left(\frac{L_1}{L_2}\right)^2}\sin(\theta) \quad (5)$$

Near the operating point (θ=90° and f=0.5), the magnitudes of he sensitivities are 0.71. As θ decreases, the system becomes less sensitive to measurement errors. The worst case measurement error sensitivity is 1.41. However these sensitivity values improve by decreasing the $L_1/L_2$ ratio.

The second property requires the measured parameters, $|^Ip_1-^Ip_2|$ and $|^Ip_3-^Ip_2|$ be sensitive to small changes in c, the distance from the image plane intersection with the diagonal fiducial to the fiducial motif origin (i.e. $c=f\sqrt{L_1^2+L_2^2}$) (FIG. 3b). This sensitivity is:

$$\frac{\partial |^Ip_1 - ^Ip_2|}{\partial c} = -csc(\theta)\sqrt{1+\left(\frac{L_1}{L_2}\right)^2} \quad (6)$$

$$\frac{\partial |^Ip_3 - ^Ip_2|}{\partial c} = -csc(\theta)\sqrt{1+\left(\frac{L_1}{L_2}\right)^2} \quad (7)$$

At the operating point of θ=90°, the magnitudes of the sensitivities are 0.71, which is the worst case for the system. As θ decreases, the sensitivity increases. Also, as discussed above, the system sensitivity improves by decreasing the $L_1/L_2$ ratio.

Applications of the localization methods of the invention are numerous. One preferred application is for percutaneous tissue biopsy within the abdominal cavity. Briefly, a patient is placed in the CT scanner and a complete set of images in the area of interest is collected. Next, while the patient remains in the scanner, the physician selects a biopsy target (e.g. a tumor) and a skin entry site from the image set. A robot, with biopsy needle and effector and fiducial object, is positioned such that the fiducial object is within the imager field of view. Next, a single image is taken, containing both the biopsy target and a cross section of the fiducial object. From this one image, the necessary translation and rotation to reach the target is determined and subsequently executed by the robot. The robot, or an attendant surgeon, can then drive the biopsy needle. Because the patient remains within the scanner, a single image will confirm that the needle has reached the target site. The biopsy is then taken, completing the procedure quickly and with minimal invasiveness.

The above discussion use includes use of a CT scanning system. However, it is understood that a variety of other three-dimensional scanning cross sectional methodologies can be employed, including use of an MRI or a scanning ultrasound.

As also discussed above, the systems and methods of the invention are suitably employed for a variety of therapeutic applications such as administration of therapeutics, administration of energy sources to a patient; energy removal from a patient; tissue removal from a patient; and the like. Potential disorders and diseases that can be treated with systems and methods of the invention include treatment of cancers (e.g. by administration of a chemotherapeutic, administration of radiation or other energy source to a tumor, surgical removal of a tumor, etc.); removal of a blockage e.g. in coronary surgery; etc.; directed or localized therapeutic administration such as for gene therapy; and the like.

All documents mentioned herein are incorporated herein in their entirety. The following non-limiting example is illustrative of the invention.

EXAMPLE 1

To determine the accuracy of the single image localization system a localization system was examined wherein the effector was a needle. The single slice determination of the needle pose, $_N^JT_{SS}$, was compared to the multislice ground truth determination of needle pose, $_N^JT_{MS}$. An average of 13 images were obtained with the robotic end effector (holder) in each of 5 different poses. All images were obtained in a GE Genesis CT Scanner wherein image slices were 5 mm thick and the image pixels were 0.7 mm by 0.7 mm. Error is defined as the difference between the multislice determined ground truth and the single slice determined pose. Components include angular error of robotic end effector 200 (holder) pose and offset error of robotic end effector (holder). From these two components, net displacement error at the needle tip, 10 cm from the center of the robotic end effector (holder) was found. The average angular error was 0.32°, the average displacement offset error was 380 microns, and the average displacement error at the needle tip was 470 microns. The displacement error probability density function was determined with a best-fit gamma distribution ($\lambda$=2.95 and $\alpha$=0.16). The maximum error seen in the 63 images was 1.45 mm with 95% of the needle tip displacement errors were below 1.0 mm.

Although a preferred embodiment of the invention has been described using specific terms, such description is for illustrative purposes only, and it is to be understood that changes and variations may be made without departing from the spirit or scope of the following claims.

What is claimed is:

1. An imaging system for invasive therapy of a patient, the system comprising:
   an imaging apparatus that can provide a cross-sectional image of a patient; and
   a medical instrument comprising a fiducial object that can be simultaneously imaged in the same image as a targeted site of the patient wherein the fiducial object comprises three N-shaped fiducial motifs each on a coplanar space, the coplanar space of each N-shaped fiducial motif being non-coplanar.

2. The system of claim 1 wherein the fiducial object representation in the image is unique for the pose of the instrument within the therapeutic field or range of motion of the instrument.

3. The system of claim 1 or 2 wherein the image can produce three identifiable points to coordinate pose of the instrument and the targeted site of the patient.

4. The system of claim 1 wherein the instrument pose is directly manipulated in reference to the medical image.

5. The system of claim 1 wherein the relative position and orientation of the medical instrument and target site of the patient can be determined from the information contained in a single cross-sectional image produced by the imaging apparatus.

6. The system of claim 1 wherein the system comprises a control apparatus that can register the instrument in a detected image space and calculate instrument movement.

7. The system of claim 6 wherein the control apparatus calculates the instrument pose in the image space by generating at least three corresponding points.

8. The system of claim 1 wherein the three N-shaped fiducial motifs are arranged orthogonally in a U-shape with one fiducial motif forming the bottom and two fiducial motifs forming the sides.

9. The system of claim 1 wherein the medical instrument is manipulated manually.

10. The system of claim 1, wherein the system further comprises a robotic apparatus capable of positioning the medical instrument.

11. The system of claim 10 wherein the instrument is positioned by the robot in the desired pose relative to the patient.

12. The system of claim 1 wherein the imaging device is a CT, MRI or ultrasound device.

13. The system of claim 1 wherein the fiducial object is affixed to the instrument.

14. The system of claim 1 wherein the fiducial object is integral to the instrument.

15. A method for guiding invasive therapy in a patient, comprising:

a) providing a system that comprises an imaging apparatus and a medical instrument comprising a fiducial object that can be simultaneously imaged in the same image as a targeted site of the patient, the fiducial object comprising three N-shaped fiducial motifs each on a coplanar space, the coplanar space of each N-shaped fiducial motif being non-coplanar;
   b) obtaining a cross-sectional image that comprises both the fiducial object and the targeted site of the patient; and
   c) manipulating the instrument with respect to the patient using information derived from the image.

16. The method of claim 15 wherein the relative position and orientation of the medical instrument and target site of the patient are determined from the information contained in a single cross-sectional image.

17. The method of claim 15 or 16 wherein the instrument is manipulated using information derived from a single reference frame of the relative position of the instrument and target site.

18. The method of claim 15 wherein the instrument is manipulated substantially contemporaneously with respect to obtaining the image.

19. The method of claim 15 wherein the instrument is manipulated based on a single image.

20. The method of claim 15 wherein a plurality of images are obtained.

21. The method of claim 20 wherein the plurality of images are taken over a period of at least one minute.

22. The method of claim 20 or 21 wherein one or more volumetric images are obtained.

23. The method of claim 15 wherein a material is deposited or administered to the patient by the instrument.

24. The method of claim 23 wherein the administered or deposited material is a therapeutic agent.

25. The method of claim 15 wherein energy is administered to the patient.

26. The method of claim 15 wherein energy is removed from the patient.

27. The method of claim 15 wherein tissue is removed from the patient by the instrument.

28. The method of claim 15 wherein the instrument administers to the patient a radiation seed implant, a DNA therapeutic, a chemotherapeutic agent, a cryotherapeutic treatment, a sclerotic solution, ethanol, high intensity ultrasound, directed beam therapy, localized X-ray therapy, photodynamic therapy, laser ablation therapy, or RF ablation therapy.

29. The method of claim 15 wherein the fiducial object representation in the image is unique for the pose of the instrument.

30. The method of claim 15 wherein the image can produce three identifiable points to coordinate pose of the instrument and the targeted site of the patient.

31. The method of claim 15 wherein the instrument pose is directly manipulated in reference to the medical image.

32. The method of claim 15 wherein the instrument is registered in detected image space by a control apparatus.

33. The method of claim 32 wherein the instrument is registered in the image space by the image generating at least three corresponding points.

34. The method of claim 15 wherein the three N-shaped fiducial motifs are arranged orthogonally in a U-shape with one fiducial motif forming the bottom and two fiducial motifs forming the sides.

35. The method of claim 15 wherein the medical instrument is manipulated manually.

36. The method of claim 15 wherein the instrument is manipulated by a robotic apparatus.

37. The method of claim 15 wherein the imaging device is a CT, MRI or ultrasound device.

* * * * *